(12) United States Patent
Talke et al.

(10) Patent No.: US 12,310,872 B2
(45) Date of Patent: May 27, 2025

(54) THUMB ORTHOSIS AND SET OF A PLURALITY OF THUMB ORTHOSES

(71) Applicants: CHW-Technik GmbH, Duderstadt (DE); Martin Talke, Berlin (DE); Matthias Roller, Balingen (DE)

(72) Inventors: Martin Talke, Berlin (DE); Matthias Roller, Balingen (DE); Helmut Wagner, Duderstadt (DE)

(*) Notice: Subject to any disclaimer, the term of this patent is extended or adjusted under 35 U.S.C. 154(b) by 649 days.

(21) Appl. No.: 17/498,450

(22) Filed: Oct. 11, 2021

(65) Prior Publication Data

US 2022/0023084 A1  Jan. 27, 2022

Related U.S. Application Data

(63) Continuation of application No. PCT/EP2020/059547, filed on Apr. 3, 2020.

(30) Foreign Application Priority Data

Apr. 12, 2019 (EP) .................................. 19 169 043

(51) Int. Cl.
*A61F 5/01* (2006.01)
*A61F 5/058* (2006.01)
*A61F 5/10* (2006.01)

(52) U.S. Cl.
CPC .............. *A61F 5/0118* (2013.01); *A61F 5/10* (2013.01); *A61F 2005/0186* (2013.01)

(58) Field of Classification Search
CPC .......... A61F 5/10; A61F 5/013; A61F 5/0118; A61F 5/05866; A61F 5/05875;
(Continued)

(56) References Cited

U.S. PATENT DOCUMENTS 4,143,653 A * 3/1979 Wichman ............ A61F 5/05875
602/22
5,584,799 A * 12/1996 Gray ................... A61F 5/05866
602/5
(Continued)

FOREIGN PATENT DOCUMENTS

DE         195 11 116 A1    9/1996
DE     20 2006 011 664 U1   11/2006
(Continued)

OTHER PUBLICATIONS

DE202014005449U1, Spörer, Jul. 25, 2014.*
(Continued)

*Primary Examiner* — Alireza Nia
*Assistant Examiner* — Andrew Jun-Wai Mok
(74) *Attorney, Agent, or Firm* — The Sladkus Law Group

(57) ABSTRACT

The invention relates to a thumb orthosis (2). The thumb orthosis (2) consists of a spreading body (1) which in particular has a bending elasticity and which serves for spreading a thumb (26) and a pointer finger (27). Furthermore, the thumb orthosis (2) comprises holding devices (22, 23) by which an end portion (28) of the spreading body (1) can be held at the thumb (26) as well as an end portion (29) of the spreading body (1) can be held at the pointer finger (27). The thumb orthosis (2) is exclusively held by the two holding devices (22, 23) at the hand (24) of the user wearing the thumb orthosis (2).

17 Claims, 14 Drawing Sheets

(58) Field of Classification Search
CPC ...... A61F 2005/0186; A61F 2007/0037; A61F 2007/0038; A41D 13/082
See application file for complete search history.

(56) References Cited

U.S. PATENT DOCUMENTS

| | | | | |
|---|---|---|---|---|
| 5,762,621 | A | * | 6/1998 | Schultz ................. A61F 5/0118 128/880 |
| 5,770,297 | A | * | 6/1998 | Grubich .................... B67B 7/18 81/3.43 |
| 6,520,925 | B1 | * | 2/2003 | Thibodo, Jr. ....... A61F 5/05875 128/880 |
| 2012/0179081 | A1 | | 7/2012 | Anglada |
| 2014/0059739 | A1 | * | 3/2014 | Gellis ................ A41D 19/0048 2/168 |
| 2015/0157483 | A1 | | 6/2015 | Grunden |
| 2016/0296359 | A1 | | 10/2016 | Stefansson |

FOREIGN PATENT DOCUMENTS

| | | | | |
|---|---|---|---|---|
| DE | 202014005449 | U1 | * 7/2014 | ............ A61F 5/0118 |
| DE | 10 2016 010 135 | A1 | 2/2017 | |
| EP | 1962746 | B1 | * 4/2011 | ............ A61F 5/0118 |
| JP | 2005-074078 | A | 3/2005 | |
| JP | 2011-194187 | A | 10/2011 | |
| JP | 2012-057286 | A | 3/2012 | |
| JP | 2017-080354 | A | 5/2017 | |
| WO | 2013/160478 | A1 | 10/2013 | |

OTHER PUBLICATIONS

Elastomers vs Polymers, Osborne, Apr. 5, 2019.*
A Study of Correlation Between Stature and Thumb Length, Prerna Chandra et al., Jun. 2016.*
Variations in the Finger Length of the Human Hand, Elizabeth Barnard et al., 1954.*
Anthropometry and Biomechanics, NASA, Jul. 1995.*
Product "Push Ortho Daumenorthese CMC" (cp. www.careshop.de).
Thumb splint of the company BORT (cp. www.bort.com).
Orthosis "Rhizo-Ring" of the company Sporlastic (cp. www. sporlastic.de).
Written Opinion of the International Searching Authority for PCT/EP2020/059547.

* cited by examiner

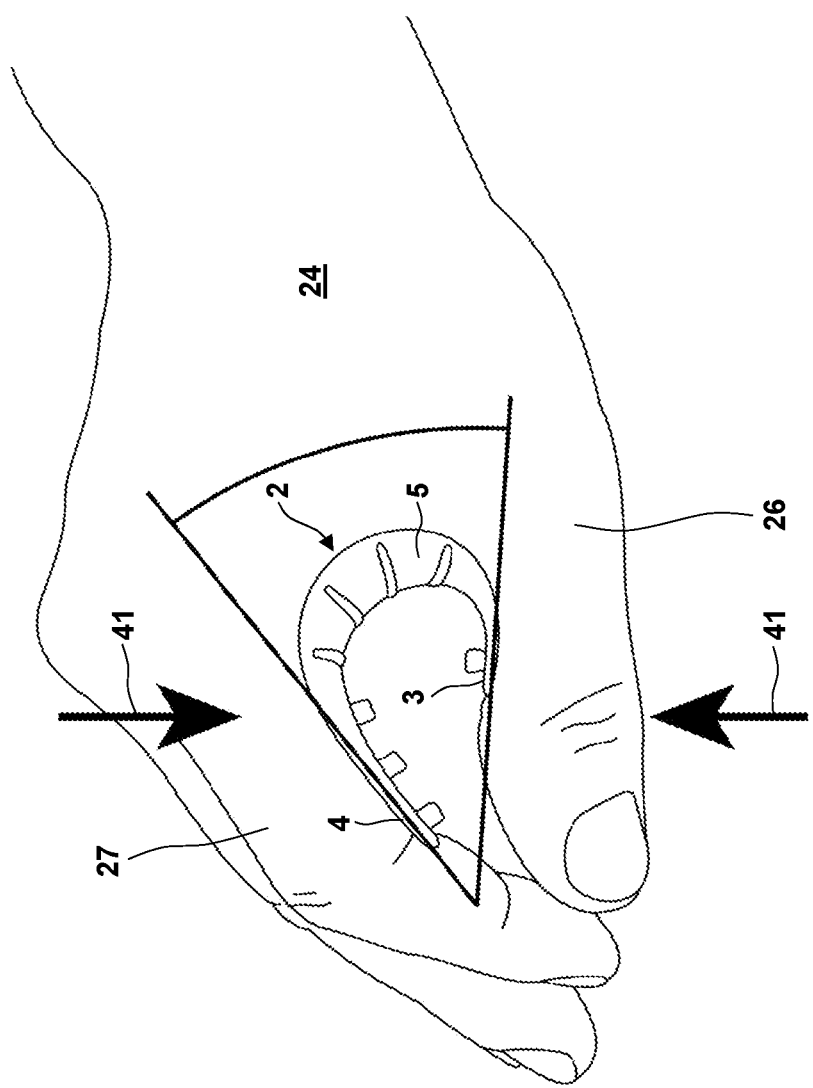

THUMB ORTHOSIS AND SET OF A PLURALITY OF THUMB ORTHOSES

CROSS REFERENCE TO RELATED APPLICATIONS

This application is a continuation of International Application PCT/EP2020/059547 with an international filing date of Apr. 3, 2020 and claiming priority to co-pending European Patent Application No. EP 19 169 043.7 entitled "Daumenorthese and Set mit mehreren Daumen-orthesen", filed on Apr. 12, 2019.

FIELD OF THE INVENTION

Thumb orthoses are in particular used for providing that a thumb of a hand is in a basic position, wherein the thumb is at least partially spread away from the pointer finger of the hand. It is e.g. possible that the use of a thumb orthosis considers the tendency of a patient having rheumatism to deposit the thumb at the pointer finger for avoiding pain. Other non-limiting examples for which the use of a thumb orthosis might be reasonable cover the therapy of chronical, posttraumatic or postoperative irritation states, pathological states in the region of associated joints, of the so-called rhizarthrosis of the thumb (arthrosis, respectively degenerative atrophy of cartilage in the region of the thumb saddle joint or carpometacarpal joint of thumb) or of a so-called skiing thumb which is caused by a brake off of the thumb in the base joint in outer direction due to a fall with a sideband rupture of the thumb. It is e.g. also possible to use the thumb orthosis for preserving the thumb joints e.g. against excessive strain or against (again) being injured, as a preventive measure or for immobilizing a carpometacarpal joint. Additional to the provision of the base position of the thumb there is the demand for thumb orthoses that the thumb orthoses provide a high wearing comfort, the thumb orthoses should (if possible) allow a pinch grip for which the tips of the thumb and the pointer finger approach each other similar to tweezers for gripping an object and that the orthosis has an appealing and (if possible) unremarkable appearance.

The present invention relates to a thumb orthosis and a set of a plurality of thumb orthoses of this type.

BACKGROUND OF THE INVENTION

DE 195 11 116 A1 discloses a thumb orthosis for correcting a malalignment of the thumb in the saddle joint. The thumb orthosis comprises a ring-shaped spreading body. The thumb is passed through the ring-shaped spreading body so that the distal end portion of the ring-shaped spreading body contacts the transition region of the hand from the thumb to the pointer finger (in the following also denoted as the "thumb bow"). The proximal end portion of the ring-shaped spreading body contacts the hand approximately in the region of the saddle joint of the thumb. In this position, the ring-shaped spreading body is secured by a holding strap. In one end region, the holding strap is fixed on the inner side of the hand to the ring-shaped spreading body. The holding strap extends around the hand in the region of the wrist. In the other end region, the holding strap is connected to the ring-shaped spreading body on the outside of the hand again. The ring-shaped spreading body is made of a thermoplastic material which might comprise a pelotte. The holding strap might be elastic and it is possible that the holding strap is tensioned by means of a hook-and-loop fastener.

Also DE 10 2016 010 135 A1 discloses a thumb orthosis comprising a ring-shaped spreading body through which the thumb is passed and comprising a holding strap wrapped around the hand above the wrist.

WO 2013/160478 A1, corresponding to US 2015/0157483 A1, discloses an orthosis by which it is possible to immobilize the thumb saddle joint and the thumb base joint. The orthosis consists of a stiff middle hand portion and a stiff thumb portion. The middle hand portion is a circular ring having a complex shape. The middle hand portion is designated for partially surrounding the hand in the region of the palm of the hand so that by means of the interaction of the middle hand portion with the hand in the region of the palm of the hand a position and orientation of the orthosis is defined. The stiff thumb portion protrudes from an end portion of the middle hand portion and comprises a thumb holding portion being ring-shaped or having the shape of a segment of a ring. It is possible to insert the thumb of the hand into the thumb holding portion in a way such that the thumb is supported against a movement towards the palm of the hand. In this way, a base position of the thumb is provided wherein the thumb and the pointer finger of the hand are juxtaposed and from which the pointer finger can be moved towards the thumb for contacting the same and can be moved away from the thumb. An individual adjustment of the orthosis to the hands of different users is allowed by a plastic deformation of the orthosis (in particular under the application of heat). The orthosis can be made from metal (in particular aluminum), from plastic or from a metal core (in particular an aluminum core) covered by plastic. The orthosis might comprise a cushion (in particular a textile cushion, a foamed cushion, a gel cushion or an air cushion) in the contact area with the hand. The orthosis might additionally be fixed by a strap having a suitable closing element. The plastic material used is in particular a thermoplastic elastomeric material.

Further thumb orthoses are known from
the publication DE 20 2006 011 664 U1,
the product "Push Ortho Daumenorthese CMC" (cp. www.careshop.de),
a thumb splint of the company BORT (cp. www.bort.com) and
an orthosis "Rhizo-Ring" of the company Sporlastic (cp. www. sporlastic.de).

Also here, a ring-shaped spreading body is fixed by holding straps which extend around the hand in the region of the wrist or the orthosis is a stiff "glove", wherein a part of the hand, the pointer finger, the middle finger, the ring finger and the small finger are left open.

JP 2017-080354 A criticizes orthoses for fixing a thumb according to the prior art described in the publications JP 2012-057286 A and JP 2005-074078 A in that these orthoses have a complex construction with a plurality of structural elements and components made of different materials, in that it is complicated to apply, hold and fix the orthoses and in that the holding function and/or fixing function is not provided in an acceptable way. Here, according to JP 2012-057286 A a kind of cut glove is used from which the finger together with a part of the hand freely extend, whereas the thumb is fixed by a sleeve through which the thumb tip passes. The sleeve has an open end. The glove can be tensioned around the hand by means of a tensioning strap. The glove comprises a plurality of complex Y-shaped reinforcing elements. Instead, the thumb orthosis known from JP 2005-074078 A comprises an inflexible sleeve-like thumb accommodation. The proximal end portion of the thumb accommodation is extended and extends up to the thumb bow and extends with a fixing section up to the wrist. A tensioning strap is fixed to the fixing section of the thumb accommodation. The tensioning strap surrounds the wrist so that in this way it is possible to fix the orthosis to the hand of the user. In order to avoid the complex construction with a number of materials and structural elements and to avoid the difficulties when applying the orthosis and fixing the same JP 2017-080354 A proposes to fix the thumb for treating a tendinitis by an orthosis having the shape of a horse saddle. The orthosis extends along the thumb bow. Along the extension of the orthosis the orthosis comprises a cross-section which is curved so that the orthosis contacts the thumb bow with curved side flanges on both sides of the thumb bow. Instead of the fixing device used in the publications JP 2012-057286 A and JP 2005-074078 A, JP 2017-080354 A proposes that the side of the thumb orthosis facing towards the thumb bow is covered by an adhesive and the thumb orthosis is adhered to the hand in the region of the thumb bow.

JP 2011-194187 A proposes a T-shaped orthosis made of an elastic plastic material. The horizontal leg of the T can be wrapped around a wrist and in the state applied to the hand the two end portions of the horizontal leg of the T can be connected to each other by a fixation means. Loop-shaped accommodating lugs for a finger of the hand extend from the free end portion of the vertical leg of the T. For another embodiment, further legs comprising further accommodating lugs for other fingers of the hand extend from the horizontal leg of the T and parallel to the vertical leg of the T (or with a small inclination relative to the vertical leg of the T).

Further prior art is known from US 2012/179081 A1 and US 2016/296359 A1.

SUMMARY OF THE INVENTION

The present invention relates to a thumb orthosis which comprises a spreading body which is used for providing a spreading of a thumb and a pointer finger, so for providing the base position. Furthermore, the inventive thumb orthosis comprises two holding devices. By means of a first holding device it is possible to hold a first end portion of the spreading body at the thumb. By means of a second holding device it is possible to hold a second end portion of the spreading body at the pointer finger. The invention proposes that the thumb orthosis is exclusively held by the two holding devices at the hand of the user wearing the thumb orthosis.

The present invention in particular proposes a thumb orthosis which is improved with respect to
the provision of a base position and/or
options for changing the position of the thumb relative to the base position and/or
the wearing comfort and/or
the constructional dimensions and/or
the optical appearance.

Furthermore, the invention proposes a set of a plurality of thumb orthoses which might be improved as explained above.

Preferably, the thumb orthosis exclusively consists of the spreading body and the holding devices which results in a notably simple design.

According to the invention, it is possible that the spreading body of the thumb orthosis exclusively or mainly extends in the intermediate space between the thumb and the pointer finger and/or in the region of the thumb bow. According to the invention, it is possible to avoid that the thumb orthosis has a design similar to a "glove" or that it is required that a holding strap extends from the spreading body around the whole hand. Instead, the thumb orthosis exclusively extends laterally from the thumb, laterally from the pointer finger and in the region of the thumb bow.

Despite of the fact that the inventive thumb orthosis provides the desired effect (namely the spreading of the thumb and the pointer finger in the intended base position), very small constructional dimensions of the thumb orthosis are given which also allows a very light design.

Furthermore, the portion of the hand covered or compromised by the thumb orthosis is reduced over the region covered by the thumb orthoses according to the prior art which also reduces impairments of the hand and which reduces the portion of the hand where the thumb orthosis is visible to the required minimum.

In some cases the material usage is reduced due to the small design of the orthosis which might lead to a reduction of the costs of the orthosis.

In the case that it is intended to fix the base position of the thumb relative to the pointer finger provided by the spreading body the spreading body might have a high stiffness. However, for one proposal of the invention the spreading body purposefully has an elasticity. Here, the elasticity of the spreading body is dimensioned such that it is possible to elastically deform the spreading body in a way such that the distance of the end portions of the spreading body can be reduced. Here, this deformation is induced by closing forces applied by the thumb and the pointer finger. The reduction of the distance of the end portions of the spreading body induced in this way leads to the result that the thumb linked to the end portion of the spreading body by the first holding device can be moved towards the pointer finger. Accordingly, despite of the use of the thumb orthosis it is possible to grip an object between the thumb and the pointer finger and also other movements of the thumb are possible. In particular, the elasticity also allows the so-called pinch grip or improves or eases the same.

Here, the spreading body might have a bending stiffness for a bending of the spreading body when reducing the distance between the thumb and the pointer finger in the main extensional plane of the spreading body which corresponds to the main extensional plane of the thumb bow (so a bending stiffness about a bending axis having an orientation vertical to the main extensional plane; according to FIG. 1 a bending axis having an orientation vertical to the drawing plane and being effective for a movement of the end portions of the spreading body in the drawing plane), the bending stiffness being higher than a bending stiffness of the spreading body for a relative movement between the thumb and the pointer finger vertical to the main extensional plane (so a bending stiffness about a bending axis lying in the main extensional plane; for FIG. 1 a bending axis which extends in the drawing plane and which is effective for a movement of an end portion of the spreading body out of the drawing plane). Alternatively or cumulatively, the spreading body might allow a relative movement between the thumb and the pointer finger for changing the distance of the same in the main extensional plane with smaller applied forces than the forces that have to be applied for a relative movement in transverse direction. In this way, it is possible that the relative movement between the thumb and the pointer finger is guided along a preferred direction with a smaller applied force, whereas transverse movements are prohibited or only possible when applying higher forces.

Generally, the spreading body might have any geometry and in particular any course, curvature or design along the longitudinal axis and/or in the cross-section. For one proposal of the invention, the spreading body comprises (in a plan view) (and in an in some cases schematic approach) a curved base leg and two side legs. The side legs each extend from an associated end portion of the base leg and diverge with an increasing distance from the base leg. Here, the curved base leg of the spreading body is designated for contacting the thumb bow. Instead, the thumb contacts a side leg, whereas the other side leg contacts the pointer finger. In the end portions of the side legs the spreading body is connected to the thumb, respectively pointer finger, by the holding devices. If the spreading body comprises an elasticity, this elasticity might be provided only in the region of the curved base leg or also in this region. Accordingly, it is possible that the base leg is deformed by forces applied by the thumb and the pointer finger so that it is possible to change the opening angle (by which in the unbiased base position the thumb is spread away from the pointer finger).

According to the invention, the spreading body extends in a way being nearly invisible and under the provision of a good guidance as well as with the provision of a contact with a large area from the thumb over the thumb bow to the pointer finger which improves the wearing comfort and/or leads to the result that the thumb orthosis is less visible and does not build an obstacle when using the hand.

Dependent on the desired base position of the thumb and the pointer finger, the side legs might have any opening angle. Preferably, the opening angle of the side leg is 60°. However, the opening angle might also differ by ±20% (in particular ±10% or ±5%) from an angle of 60°. It has shown that an opening position of the pointer finger and the thumb provided in this range guarantees a good therapeutic effect, where in some cases a so-called "pinch grip" still remains possible.

The spreading body might have any cross-section (which might be constant or might change over the spreading body). For a particular proposal, the spreading body might have a curved cross-section. Here, the curved cross-section in particular has a concave shape in the contact area with the thumb, the thumb bow and/or the pointer finger on the side facing towards the thumb, the thumb bow and/or the pointer finger so that the cross-section might partially enclose or accommodate the thumb, the thumb bow and/or the pointer finger. The coverage or partial encirclement on the one hand leads to an increase of the contact area so that impairments of the skin and pressure peaks are avoided. On the other hand, the accommodation of the thumb, the thumb bow and/or the pointer finger with a positive form lock in the concave curved cross-section of the spreading body due to the partial enclosing leads to a good guidance and/or fixation of the thumb orthosis relative to the thumb, the thumb bow and/or the pointer finger.

For the manufacturing of the spreading body it is e.g. possible to use any material, material mixture or composite material. For one proposal of the invention, the spreading body is manufactured from plastic which is e.g. provided in an injection molding process.

For the design of the holding device by which the spreading body is fixed to the thumb, respectively the pointer finger, there are lot of options. Here also holding devices known from the prior art can be used. For one proposal of the invention, at least one holding device comprises a (e.g. flexible, elastic and/or form-stable) holding strap. The holding strap is at least partially looped around the associated thumb or pointer finger. The holding strap might also completely enclose the thumb or the pointer finger in a ring-shape. It is also possible that starting from the spreading body the holding device comprises two holding straps or one holding strap with two holding strap portions which extend in opposite circumferential directions from the spreading body around the thumb or the pointer finger.

Within the frame of the invention, there are a lot of options for the design of the holding straps. In order to mention only some options, the holding strap might be a holding strap which can be elastically deformed in longitudinal direction and/or might be a holding strap which is elastically bendable (e.g. a holding strap made of rubber). The elasticity is then used for providing a tensioning of the holding device at the thumb or pointer finger for increasing the holding effect holding the thumb orthosis at the hand. It is also possible that a holding strap is used which can be plastically deformed (in some cases under the application of heat). By means of the plastic deformation it is possible to adapt the generally form-stable holding strap to the size and/or geometry of the thumb or the pointer finger of different users. It is also possible that a holding strap is used which can be plastically deformed for an adaptation to different users and that then still a certain elasticity is provided for providing a good (and in some cases close or tight) holding connection between the thumb or the pointer finger and the holding strap. It is also possible that a textile holding strap is used or a strap with a hook-and-loop fastener.

For one embodiment of the inventive thumb orthosis, the end portions of a holding strap of the holding device or of two holding straps of the holding device can be connected to each other by a connecting device. Here, the connecting device preferably allows a connection of the two end portions in different relative position so that it possible that the holding device can be put on the thumb or the pointer finger and that dependent on the relative position an adaptation to different dimensions of a thumb or a pointer finger is possible or it is possible to induce different tensions at the thumb or the pointer finger. If the holding strap forms a ring, by the different relative positions of the connecting device wherein the two end portions are connected to each other it is possible to adjust the diameter of the provided ring. In order to mention some non-limiting examples, the connecting device might be embodied as a hook-and-loop fastener. However, it is also possible that the connecting device comprises a plugging element (e.g. a mushroom head) formed by an end portion of a holding strap or the spreading body. Furthermore, the connecting device comprises a recess formed by the holding strap (in particular in an end region of the same). The plugging element is inserted into the recess for the provision of the connection. For the mentioned example of the mushroom head, the recess might be a bore or hole of the holding strap. The mushroom head (which is in particular carried by the spreading body) can be inserted or plugged into the bore or hole. It is also possible that recesses in both end portions of the holding strap can be connected by the mushroom head. In the case that different relative positions should be provided, a plurality of plugging elements and/or recesses can be arranged along the longitudinal extension of the holding strap.

For the type of coupling of the holding devices to the spreading body there are a lot of options. In the simplest case, the spreading body is fixedly connected to the holding device, e.g. by a material bond, by stitching, adhering or screwing and the like. The invention also proposes that the holding device is connected to the spreading body by a coupling device. This coupling device might e.g. be releasable so that in some cases it is possible that one and the same holding device can be used with different spreading bodies (e.g. spreading bodies having different dimensions and/or different stiffnesses). In some cases, a releasable coupling device also allows a different way of application of the orthosis by at first connecting the holding device to the thumb and the pointer finger and then connecting the spreading body to the holding devices by the coupling devices. Alternatively or cumulatively, it is possible that the coupling device provides a degree of freedom. It is e.g. possible that for an elastic embodiment of the spreading body the elastic deformation of the spreading body has the effect that there is a relative movement between the hand and the spreading body. If in this case the holding device is connected without any degree of freedom of the coupling device to the spreading body, this might lead to an excoriation of the thumb or the pointer finger due to the contact with the holding device. For avoiding any such excoriation, a displacement degree of freedom of the coupling device allows a compensating movement so that despite of the elastic deformation of the spreading body the contact area of the holding device with the thumb and the pointer finger does not change and no frictional forces are generated in the contact area.

For a particular proposal, the spreading body comprises a guiding element (in particular on the side facing away from the thumb, the thumb bow or the pointer finger). By means of the guiding element a guidance of an object carried or gripped by the hand equipped with the thumb orthosis can be provided. The guiding element might e.g. be a guiding rib, a guiding protrusion or a guiding recess. If it is e.g. of interest to write with the hand carrying the thumb orthosis, usually the used pencil is brought into contact with the thumb bow of the hand. By the contact force of the thumb bow at the pencil a fixation and a definition of the orientation of the pencil can be provided. If instead the pencil contacts the spreading body, the fixation and definition of the orientation might be reduced. In this case, a support of the pencil with a positive form lock can be provided by a guiding element as e.g. a guiding rib so that the process of writing with the pencil can be eased.

Generally, any shape and dimensions of the inventive thumb orthosis and in particular of the spreading body can be used. Preferably, the dimensions of the thumb orthosis are adapted to the size of the hand of the user. It is also possible that thumb orthoses are provided with a limited number of different dimensions which are then designated for associated sizes of the hands in specific dimensional regions.

For one proposal of the invention, the thumb orthosis is dimensioned as follows:
a) For one proposal of the invention, the spreading body comprises a curved base leg, the curved base leg having a radius of curvature of 25 mm. Due to the fact that the curved base leg is designated for the contact with the transition or thumb bow, the radius of curvature of 25 mm corresponds to the radius of curvature of the thumb bow.
b) Alternatively or cumulatively, the spreading body comprises a first side leg which is designated for the contact with the thumb. The length of this first side leg is 11 mm.
c) Alternatively or cumulatively, the spreading body comprises a second side leg having a length of 30 mm. The second side leg is (as explained above) designated for the contact with the pointer finger.
d) Alternatively or cumulatively, the spreading body comprises a cross-section with a radius of curvature of 18 mm in the region of the first side leg. This radius of curvature generally corresponds to the diameter of a thumb in the contact region of the first side leg.
e) Alternatively or cumulatively, the spreading body comprises a cross-section having a radius of curvature of 37 mm in the region of the second side leg which approximately corresponds to the radius of curvature of the pointer finger.
f) Alternatively or cumulatively, the spreading body might have a radius of curvature of 12 mm in the region of the base leg which is designated for contacting the thumb bow.

The aforementioned dimensions are preferably usable for a hand where the thumb bow for spread pointer finger and thumb comprises a radius of 25 mm±3 mm or 25 mm±2 mm or 25 mm±1 mm. With a corresponding scaling adapted dimensions can be used for different hand sizes. Within the frame of the invention also deviations from the given lengths and/or radii of ±50%, ±20%, ±10% or ±5% are possible. Here, the above specified dimensions a) to f) might all or only partially be embodied in a thumb orthosis.

As mentioned before, thumb orthoses having different dimensions can be provided for different hands. For one proposal of the invention, an existing thumb orthosis can be adapted by changing the length of at least one side leg of the spreading body and/or by changing the size of a holding device or the length of at least one holding strap. Here, it is possible that the length is changed by a predetermined separation point (in particular a material weakening) of the side leg of the spreading body or of the holding strap. In the case that it shows that for a hand that is to be equipped with the thumb orthosis the side leg of the spreading body is too long, the side leg can be shortened by severing or braking of the predetermined separation point. The corresponding applies for the holding strap. By the separation of excess material portions the optical appearance of the thumb orthosis can be improved, the weight of the thumb orthosis can be reduced to the required extent and interferences of protruding material portions can be avoided.

Another solution of the object of the invention is a set comprising a plurality of different thumb orthoses. Such a set of different thumb orthoses might e.g. be provided by a manufacturer or also be held on stock by a specialized shop for orthopedic products so that for customers having hands of different sizes a suitable thumb orthosis can be selected. In the set of the plurality of thumb orthoses the different thumb orthoses have different dimensions for hands of different sizes.

Alternatively or cumulatively, it is possible that the different thumb orthoses of the set have spreading bodies with different elasticities. In this way, it is possible that a thumb orthosis with a spreading body having a very low elasticity is chosen when a fixation of the thumb is desired, whereas dependent on the extent of the desired flexibility of the spreading body spreading bodies having a larger elasticity can be used. It is also possible that by the choice of the elasticity of the spreading body hand forces that can be generated by the hand of different patients can be considered.

Advantageous developments of the invention result from the claims, the description and the drawings. The advantages of features and of combinations of a plurality of features mentioned at the beginning of the description only serve as examples and may be used alternatively or cumulatively without the necessity of embodiments according to the invention having to obtain these advantages. Without changing the scope of protection as defined by the enclosed claims, the following applies with respect to the disclosure of the original application and the patent: further features may be taken from the drawings, in particular from the illustrated designs and the dimensions of a plurality of components with respect to one another as well as from their relative arrangement and their operative connection. The combination of features of different embodiments of the invention or of features of different claims independent of the chosen references of the claims is also possible, and it is motivated herewith. This also relates to features which are illustrated in separate drawings, or which are mentioned when describing them. These features may also be combined with features of different claims. Furthermore, it is possible that further embodiments of the invention do not have the features mentioned in the claims.

The number of the features mentioned in the claims and in the description is to be understood to cover this exact number and a greater number than the mentioned number without having to explicitly use the adverb "at least". For example, if an element is mentioned, this is to be understood such that there is exactly one element or there are two elements or more elements. Additional features may be added to these features, or these features may be the only features of the respective product.

The reference signs contained in the claims are not limiting the extent of the matter protected by the claims. Their sole function is to make the claims easier to understand.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 17 schematically shows a determination of a stiffness of a thumb orthosis.

DETAILED DESCRIPTION

Figure 1:
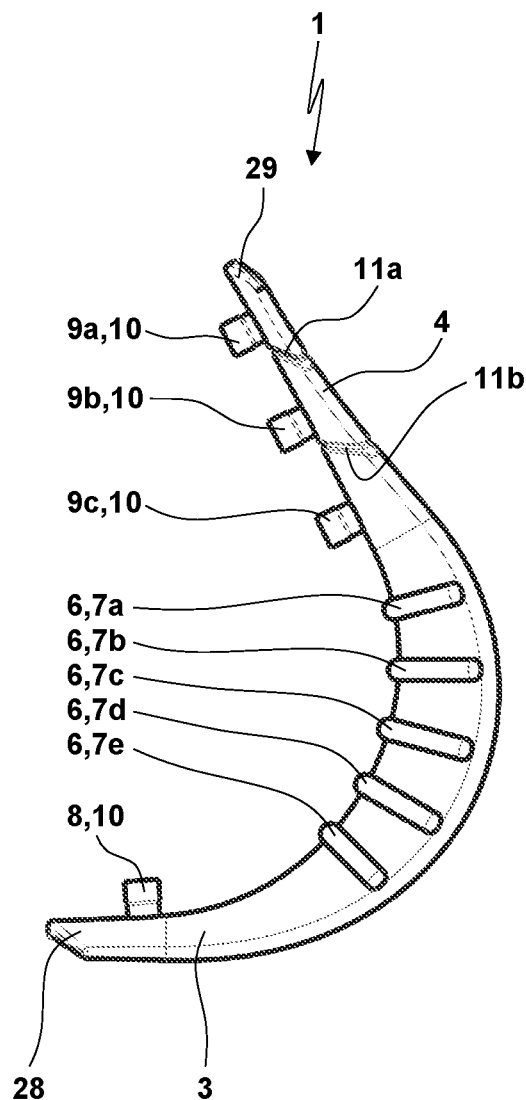
FIGS. 1 to 7 show different views of a spreading body of a thumb orthosis where possible dimensions of the spreading body can be taken from FIGS. 4 to 7.
Figure 2:
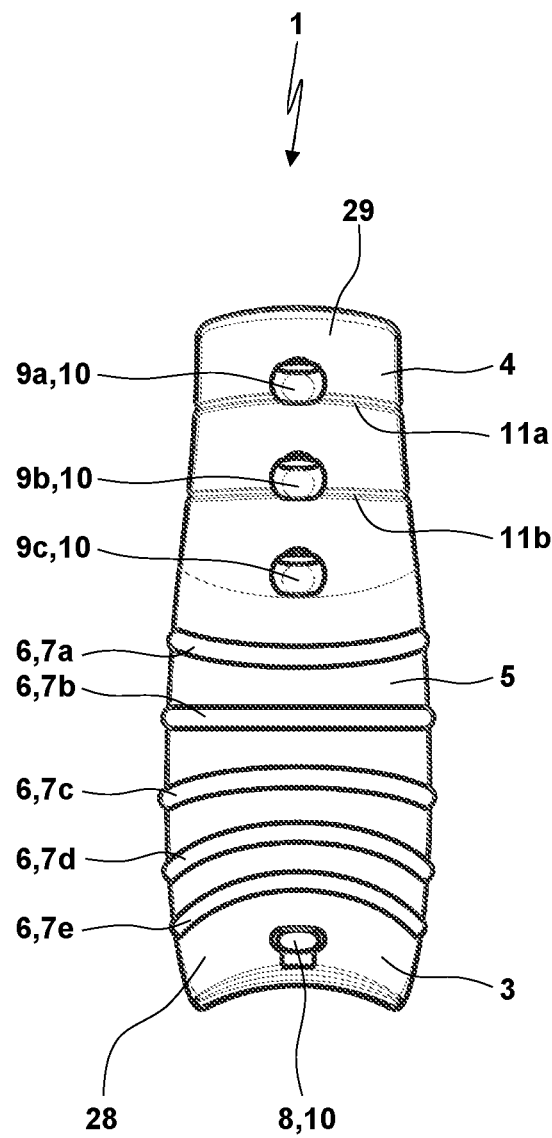
Figure 3:
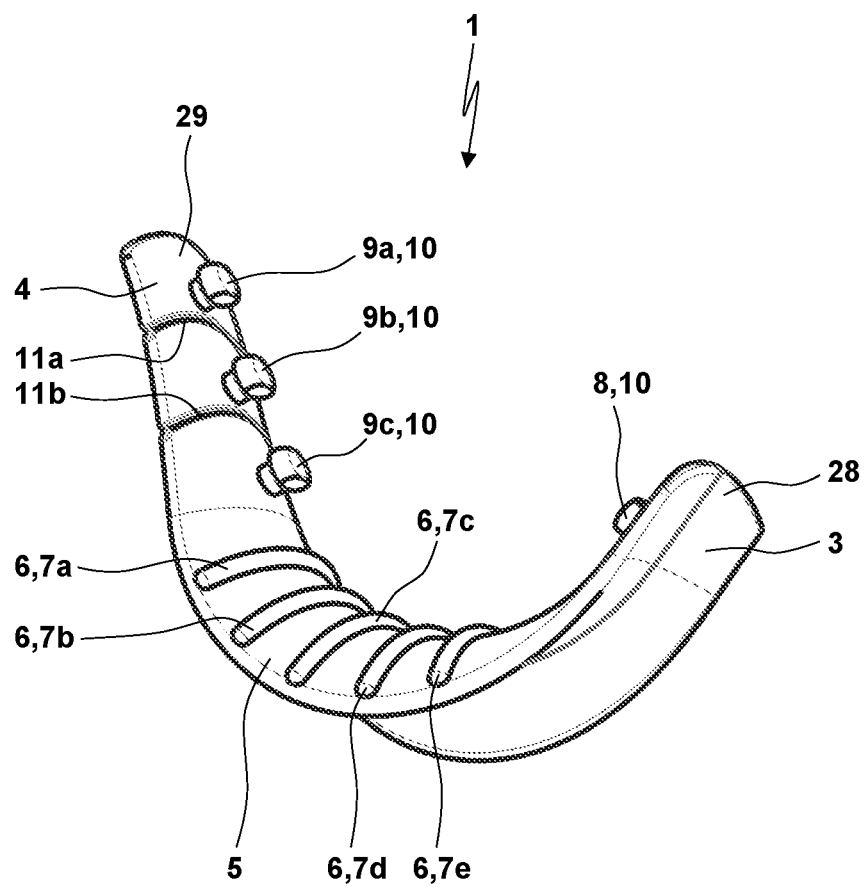
Figure 4:
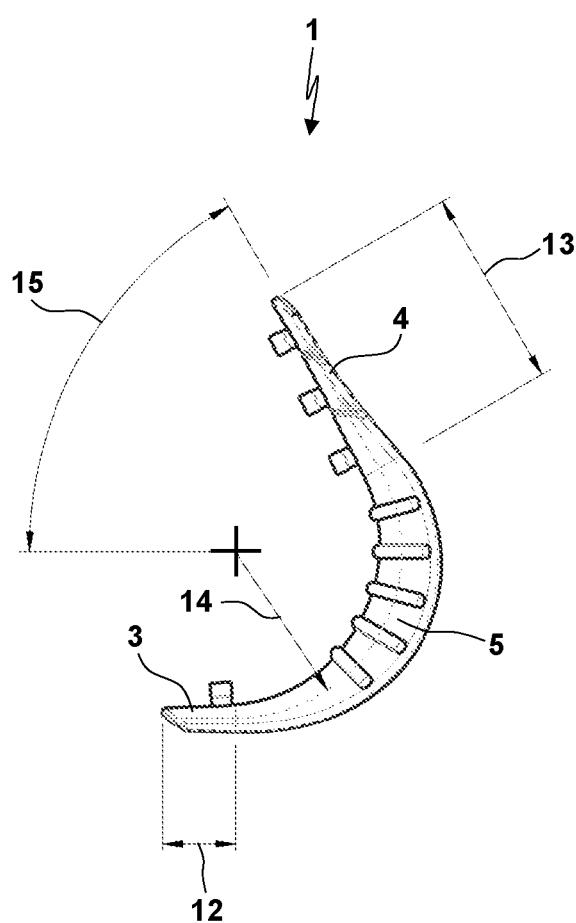
Figure 5:
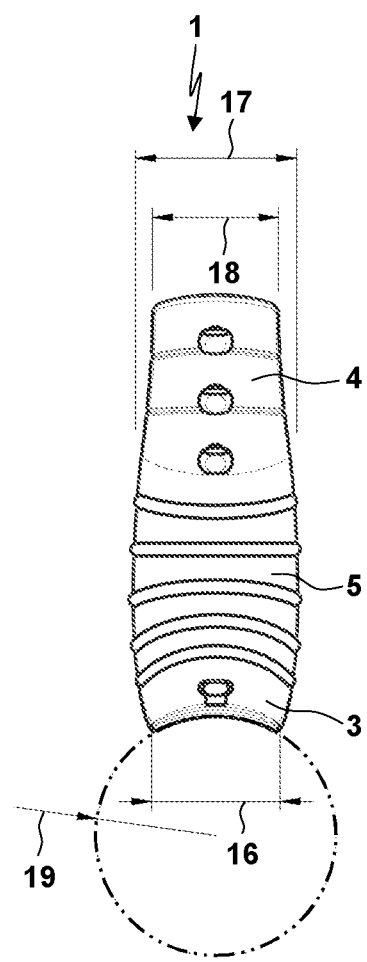
Figure 6:
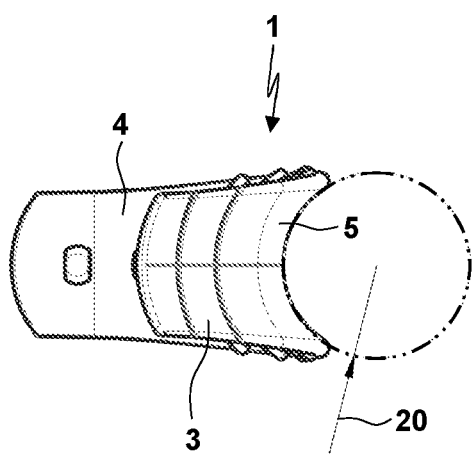
Figure 7:
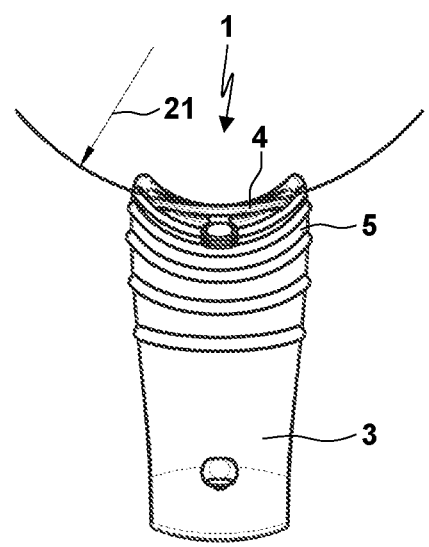

Referring now in greater detail to the drawings, FIGS. 1 to 7 show a spreading body 1 of a thumb orthosis 2. The spreading body 1 comprises (in the plan view of FIG. 1) two generally straight side legs 3, 4. The side legs 3, 4 are connected to each other by a curved base leg 5. The spreading body 1 has a curved or domed cross-section such that the spreading body 1 has a concave shape in the contact area with the hand.

Here, the concave curvature of the cross-section changes along the longitudinal extension from the side leg 3 via the base leg 5 to the side leg 4. The transverse extension along the curvature also changes along the longitudinal extension of the spreading body 1. The transverse extension of the spreading body 1 is larger in the region of the curved base leg 5 than in the region of the side legs 3, 4. Preferably, the transverse extension of the spreading body 1 continuously decreases from the maximal width approximately in the middle of the base leg 5 to the free end portions of the side legs 3, 4. Optionally, the spreading body 1 might comprise guiding elements 6 (here guiding ribs 7a, 7b, 7c, 7d, 7e) on the side which does not contact the hand.

Optionally, the spreading body 1 comprises at least one coupling device 8, respectively 9a, 9b, 9c, in the region of the side leg 3 and/or in the region of the side leg 4. For the shown embodiment, the coupling devices 8, 9 are embodied as mushroom heads 10 integrally formed by the spreading body 1.

It is possible that predetermined separation points 11a, 11b are provided in the region of at least one side leg 3, 4. The predetermined separation points 11a, 11b allow a reduction of the length of the associated side legs 3, 4. It is possible that by shortening the length of a side leg 3, 4 also a coupling device 9a, 9b is separated. For the shown embodiment, the predetermined separation points 11a, 11b are embodied as material recesses or material weakenings embodied as grooves.

In FIGS. 4 to 7 optional dimensions of the spreading body 1 are shown. The length 12 of the side leg 3 can be 11 mm, whereas the length 13 of the side leg 4 can be 30 mm. The radius of curvature 14 of the base leg 5 can be 25 mm. An opening angle 15 of the two side legs 3, 4 can be 60° which can be provided by the corresponding circumferential angle and the curvature of the base leg 5. The transverse extension of the spreading body 1 changes over the longitudinal extension. The smallest transverse extension 16 of the side leg 3 in its free end portion can be 19 mm, whereas the largest transverse extension 17 of the base leg 5 can be 24 mm and the smallest transverse extension 18 of the side leg 4 in its free end portion can be 19 mm. The transverse extension changes continuously between these minimal and maximal transverse extensions 16, 17, 18. In the region of the side leg 3 the cross-section of the spreading body 1 is curved with a radius of curvature 19 which might be 19 mm. In the region of the base leg 5 the radius of curvature 20 might be 12 mm. In the region of the side leg 4 the radius of curvature 21 can be 37 mm.

Dependent on the size of the hand, of the thumb, of the pointer finger and/or of the thumb bow the dimensions can be adapted. The aforementioned dimensions preferably apply for a hand size 25. It is possible that the opening angle 15 differs by ±20° (preferably ±15° or ±10° or ±5°) from the given opening angle of 60°. The other dimensions might differ from the given dimensions by ±50%, ±20%, ±15%, ±10% or ±5%.

FIGS. 8 to 11 show a thumb orthosis 2 consisting of the spreading body 1 according to FIGS. 1 to 7 and holding devices 22, 23 mounted to the ends of the spreading body 1. FIGS. 8 to 11 show the thumb orthosis 2 in a state applied to a hand 24. Here, the spreading body 1 contacts the transition from the thumb 26 to the pointer finger 27 (which is here also named and denoted thumb bow 25) with the concave curved or domed inner side of the base leg 5. Due to the concave curvature or domed shape of the side of the spreading body 1 facing towards the thumb bow 25, the cross-section of the base leg 5 partially encloses the thumb bow 25. Said in different words, the thumb bow 25 enters into the concave recess of the base leg 5.

The thumb 26 contacts the side leg 3. Preferably, the length of the side leg 3 is dimensioned such that the side leg 3 approximately extends up to the foremost thumb joint or ends shortly before the foremost thumb joint. Due to the concave curvature or domed shaped of the side leg 3, the side leg 3 also partially encloses the thumb 26 with its cross-section.

The pointer finger 27 contacts the side leg 4. Due to the concave curvature or domed shape of the side of the side leg 4 facing towards the pointer finger 27, the cross-section of the side leg 4 partially encloses the pointer finger 27. Preferably, the length of the side leg 4 is dimensioned such that the side leg 4 approximately extends up to the second foremost joint of the pointer finger 27 or ends shortly before the second-foremost joint of the pointer finger 27.

In a free end portion 28 the side leg 3 carries the holding device 22. In a corresponding way, a free end portion 29 of the side leg 4 carries the holding device 23.

The holding devices 22, 23 each comprise a holding strap 30, 31. The holding strap 30 has a ring- or loop-shaped design and completely surrounds the thumb 26. With an (in particular elastic) pretension the holding strap 30 presses the side leg 3 against the thumb 26. The corresponding applies for the holding strap 31 and the pointer finger 27.

Figure 8:
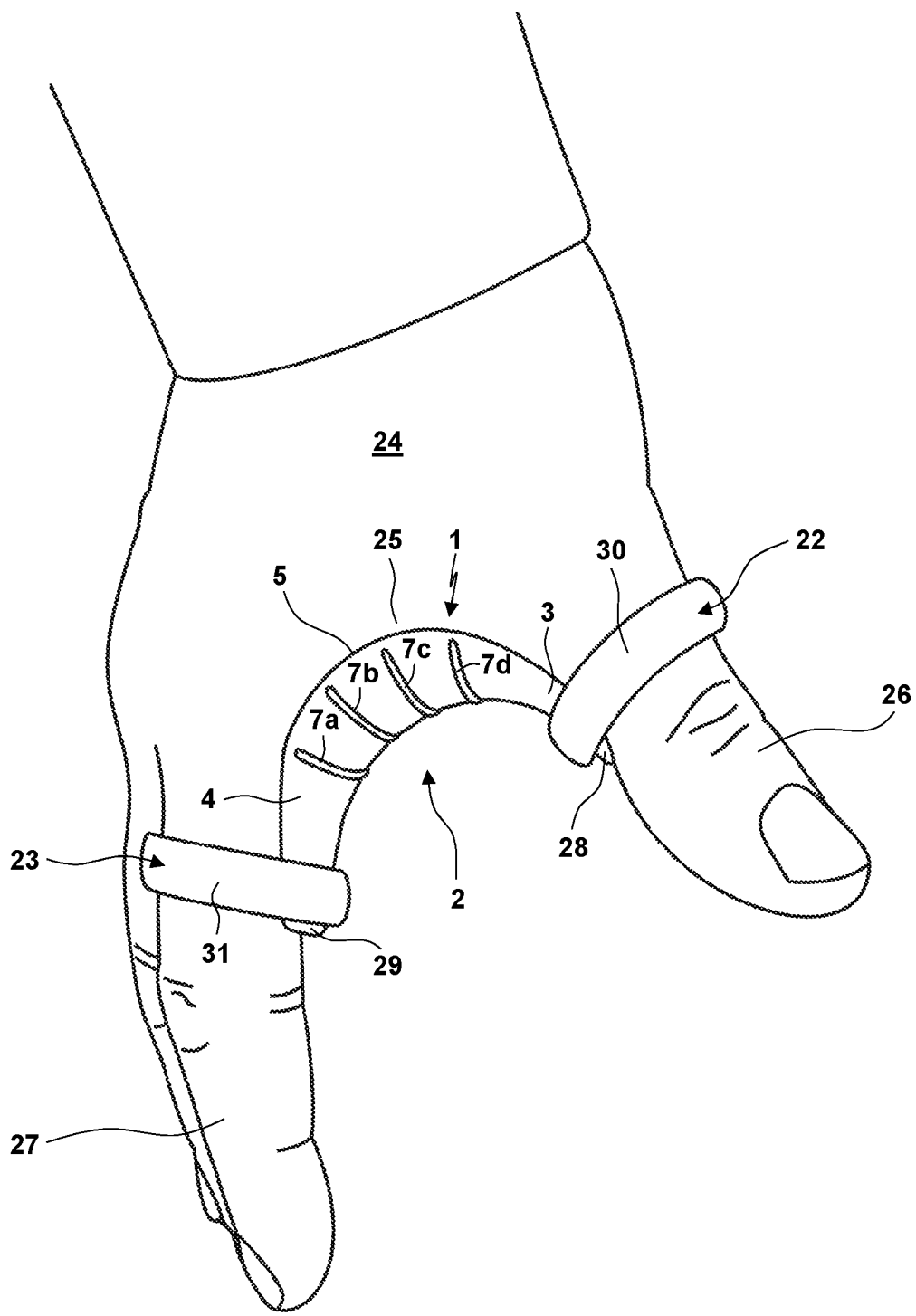
FIGS. 8 to 11 show a thumb orthosis comprising a spreading body according to FIGS. 1 to 7 and with holding devices in a state applied to the hand in different operational positions.

FIG. 8 shows the hand 24 with the thumb orthosis 2 in an applied state. Here, the user does not apply a force to the thumb 26 and the pointer finger 27. Accordingly, the orientation of the thumb 26 and the pointer finger 27 is defined by the spreading body 1 corresponding to the opening angle 15 so that a base position is provided.

Figure 9:
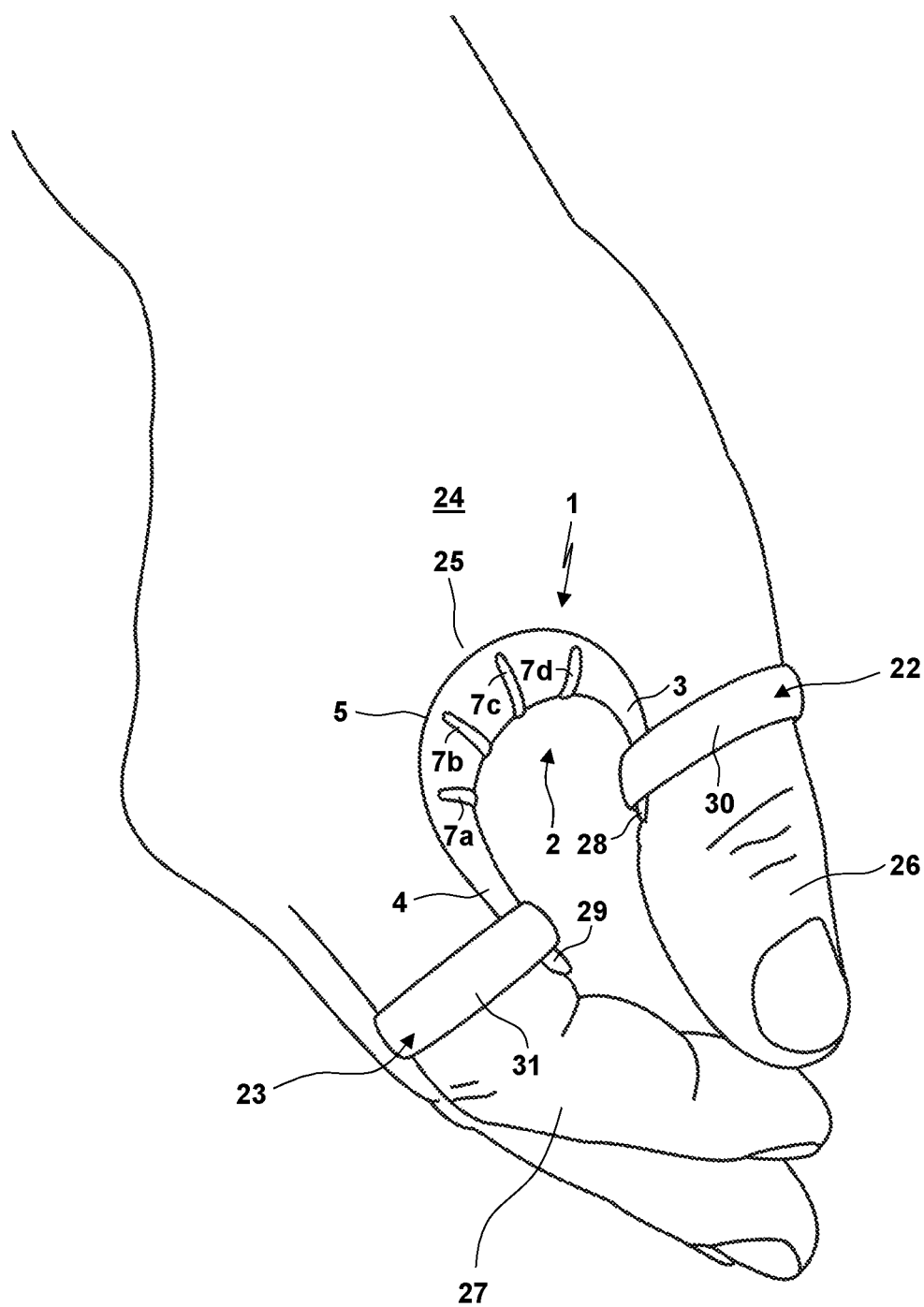

FIG. 9 shows the thumb orthosis 2 in a state wherein the spreading body 1 is elastically deformed because the user generates forces which move the thumb 26 towards the pointer finger 27. The generated forces lead to the elastic deformation of the spreading body, in particular in the region of the base leg 5, so that the opening angle 15 reduces and the distance of the thumb 26 from the pointer finger 27 (in the region of its contact area with the side legs 3, 4) can be reduced. FIG. 9 shows the so-called "pinch grip". Here, it is possible that the opening angle of 60° in the base position changes due to the applied forces up to 10°, 0° or even according to FIG. 9 to a negative angle in a way such that the side legs 3, 4 no longer diverge but converge.

Figure 10:
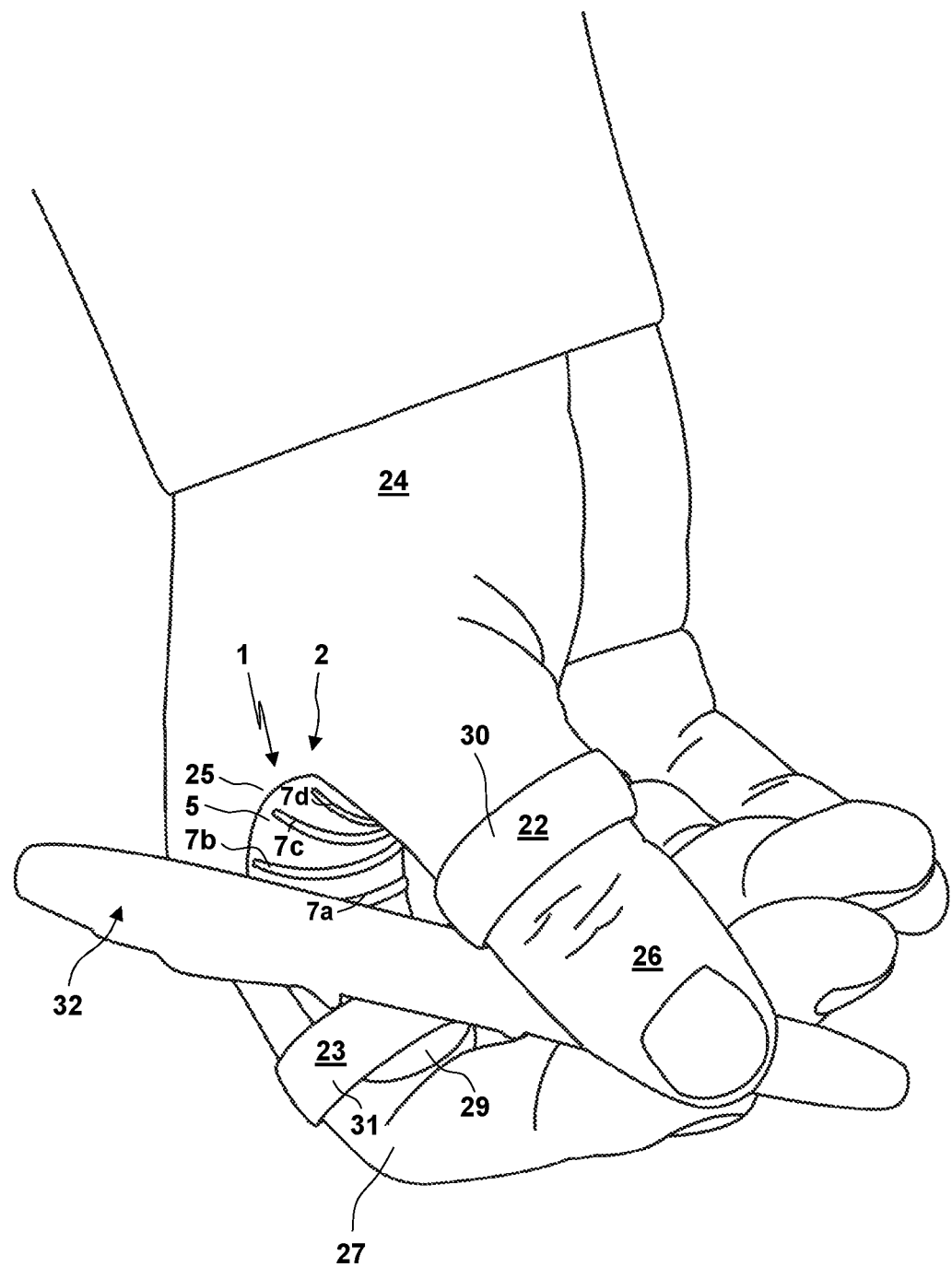

FIG. 10 shows the use of the thumb orthosis 2 for writing with a pencil 32. It can be seen that the pencil 32 contacts the guiding ribs 7 and the pencil 32 is guided by the guiding ribs 7 with a positive form lock.

Figure 11:
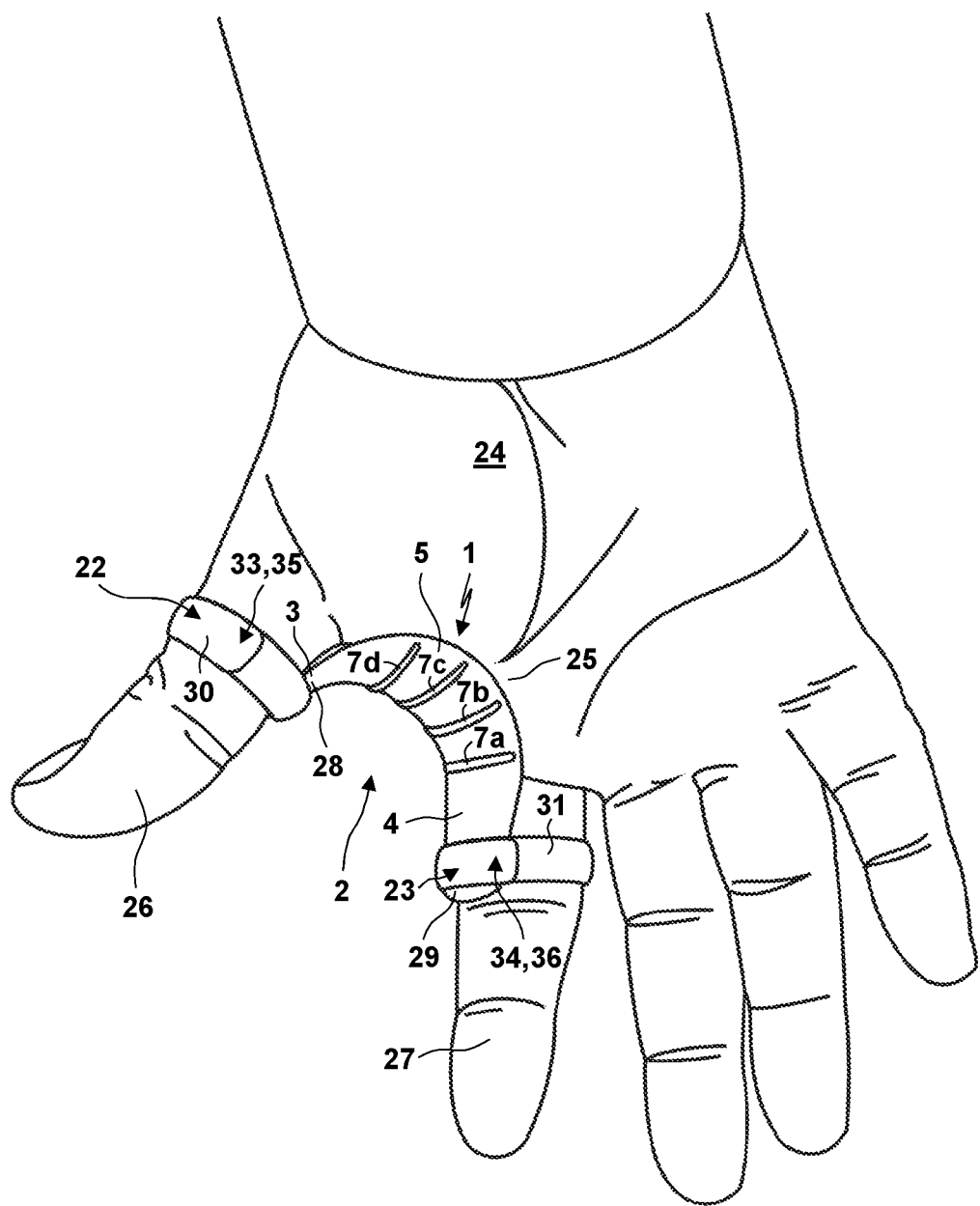

For the embodiment shown in FIG. 11, the holding straps 30, 31 are connected at their ends to each other by means of connecting devices 33, 34 which are here embodied as hook-and-loop fasteners 35, 36. By means of the hook-and-loop fasteners 35, 36 it is possible to close the holding straps 30, 31 tight around the thumb 26, respectively the pointer finger 27. In this case, the holding straps 30, 31 are embodied as textile straps or hook-and-loop straps which are fixedly connected to the spreading body 1 (e.g. by stitching or adhering).

Figure 12:
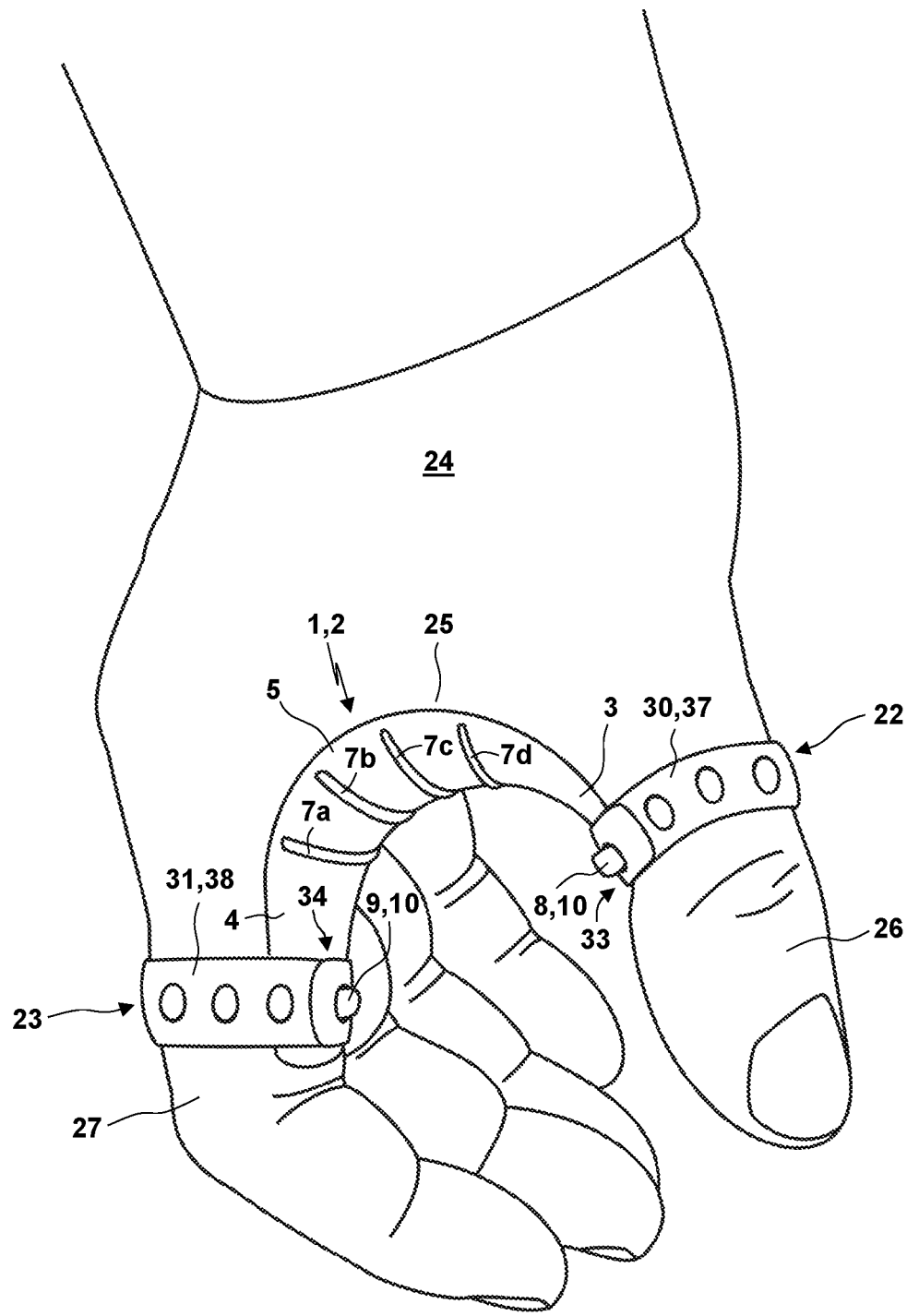
FIGS. 12 to 14 show thumb orthoses with different designs of the holding devices in the applied state.

For the embodiment shown in FIG. 12, the holding straps 30, 31 are embodied as punched straps 37, 38. Preferably, in this case the holding straps 30 are elastic, in particular embodied as rubber straps. One hole in an end portion of the holding strap 30, 31 is then plugged on a mushroom head 10 of the spreading body 1 and after wrapping the holding strap around the thumb 26, respectively the pointer finger 27, in the region of another hole another end portion of the holding strap is plugged onto the mushroom head 10. Due to the fact that the holding straps 30, 31 comprise a plurality of holes distributed over the longitudinal extension, dependent on the choice of the hole used for plugging onto the mushroom head 10, an adaptation to different diameters of the thumb 26, respectively the pointer finger 27 and/or to different desired pressing forces is possible. It is possible that also the holding straps 30, 31 comprise predetermined separation points by which it is then possible to cut an excess length of the holding straps 30, 31.

Figure 13:
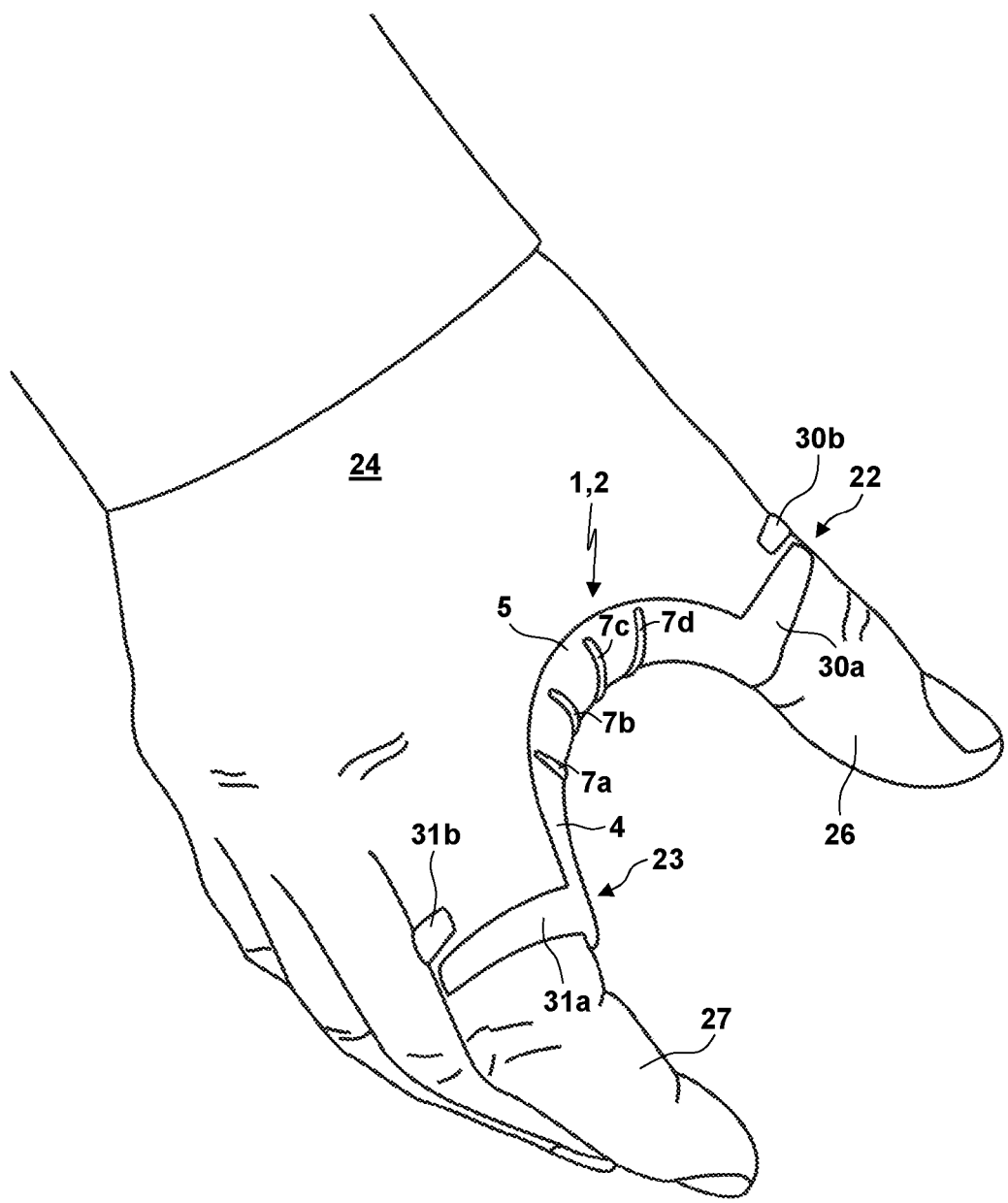

FIG. 13 shows a different embodiment of the holding devices 22, 23. Here, the holding straps 30, 31 are not flexible but have an own rigidity. In this case, holding straps 30a, 30b, respectively 31a, 31b, extend from the base body of the spreading body 1 in different circumferential directions around the thumb 26, respectively the pointer finger 27. For the shown embodiment, the holding straps 30a, 30b, respectively 31a, 31b, are passed besides one another, so that they comprise an overlap (without this necessarily being the case). The holding straps 30a, 30b, respectively 31a, 31b, have an elasticity. The shape having the own stiffness is chosen such that when inserting the thumb 26, respectively the pointer finger 27, the holding straps 30a, 30b, respectively 31a, 31b, are elastically widened. Accordingly, in the applied state the holding straps 30a, 30b, respectively 31a, 31b, are pressed to the thumb 26, respectively the pointer finger 27, and in this way the thumb orthosis 2 is fixed to the hand 24. Here, it is possible that (as shown in FIG. 13) the holding straps 30a, 30b, 31a, 31b, are integrally connected as one piece to the spreading body 1 which is e.g. possible when manufacturing the spreading body 1 together with the holding straps 30a, 30b, 31a, 31b in an injection molding process.

Figure 14:
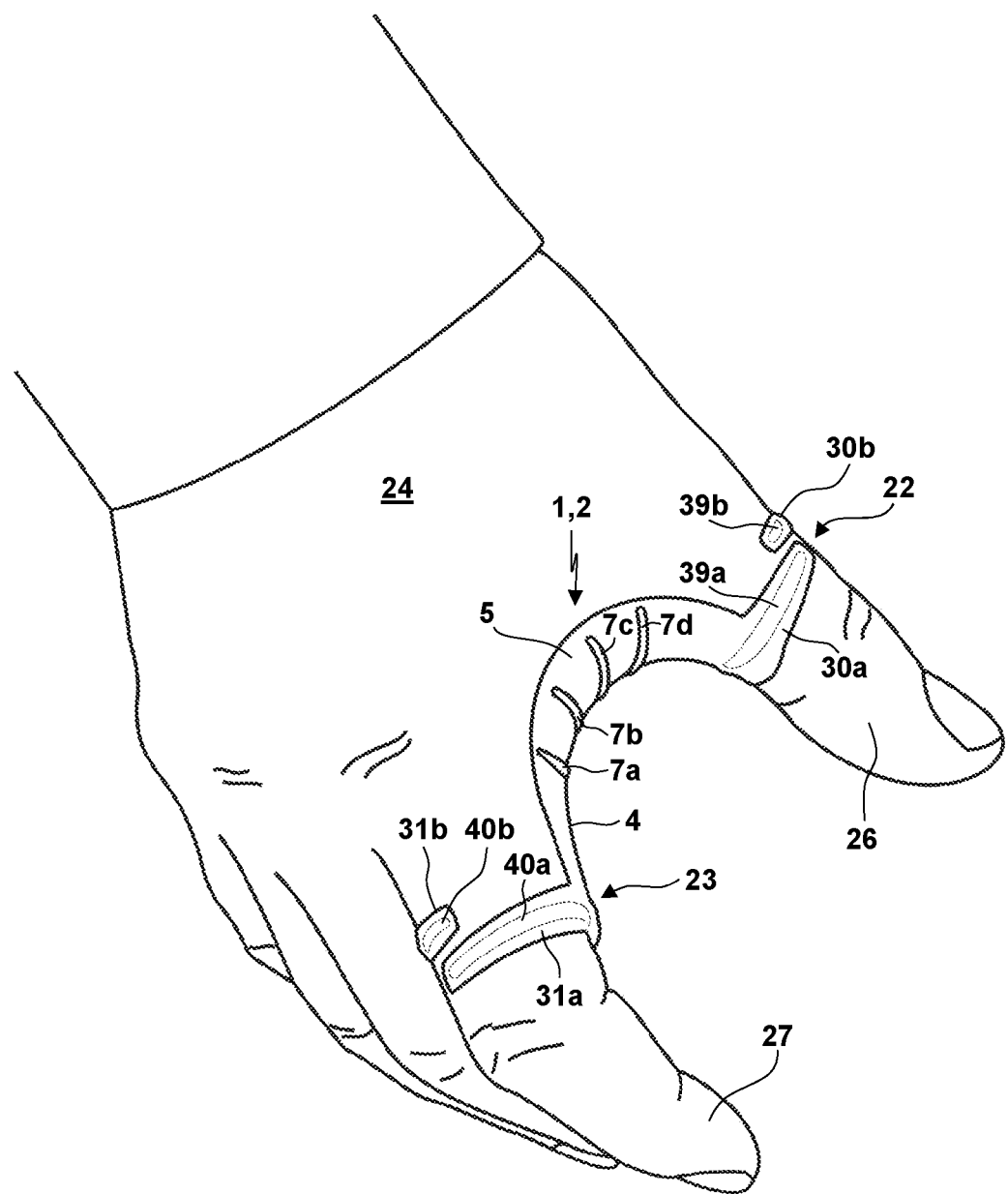

It is also possible that the holding straps 30a, 30b, 31a, 31b are embodied as a composite body. FIG. 14 shows an embodiment wherein metal bands 39a, 39b, 40a, 40b are embedded into the holding straps 30a, 30b, 31a, 31b (e.g. manufactured from plastic). The metal bands 39a, 39b, 40a, 40b allow a plastic deformation for an adaptation to the hand 24 and on the other hand provide any required elasticity.

Figure 15:
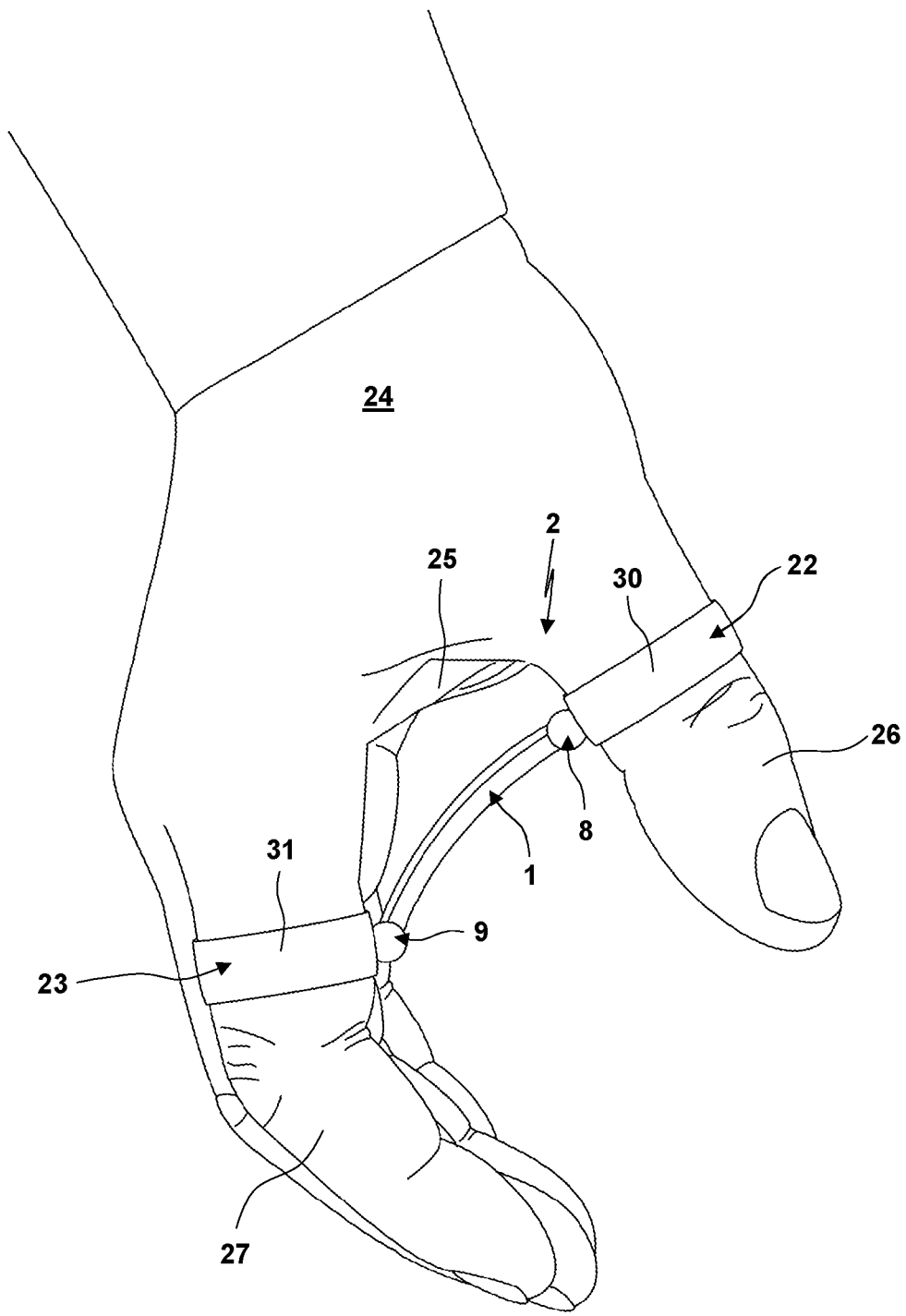
FIGS. 15 and 16 show another embodiment of a thumb orthosis comprising a spreading body which does not extend along the thumb bow but between the thumb and the pointer finger.
Figure 16:
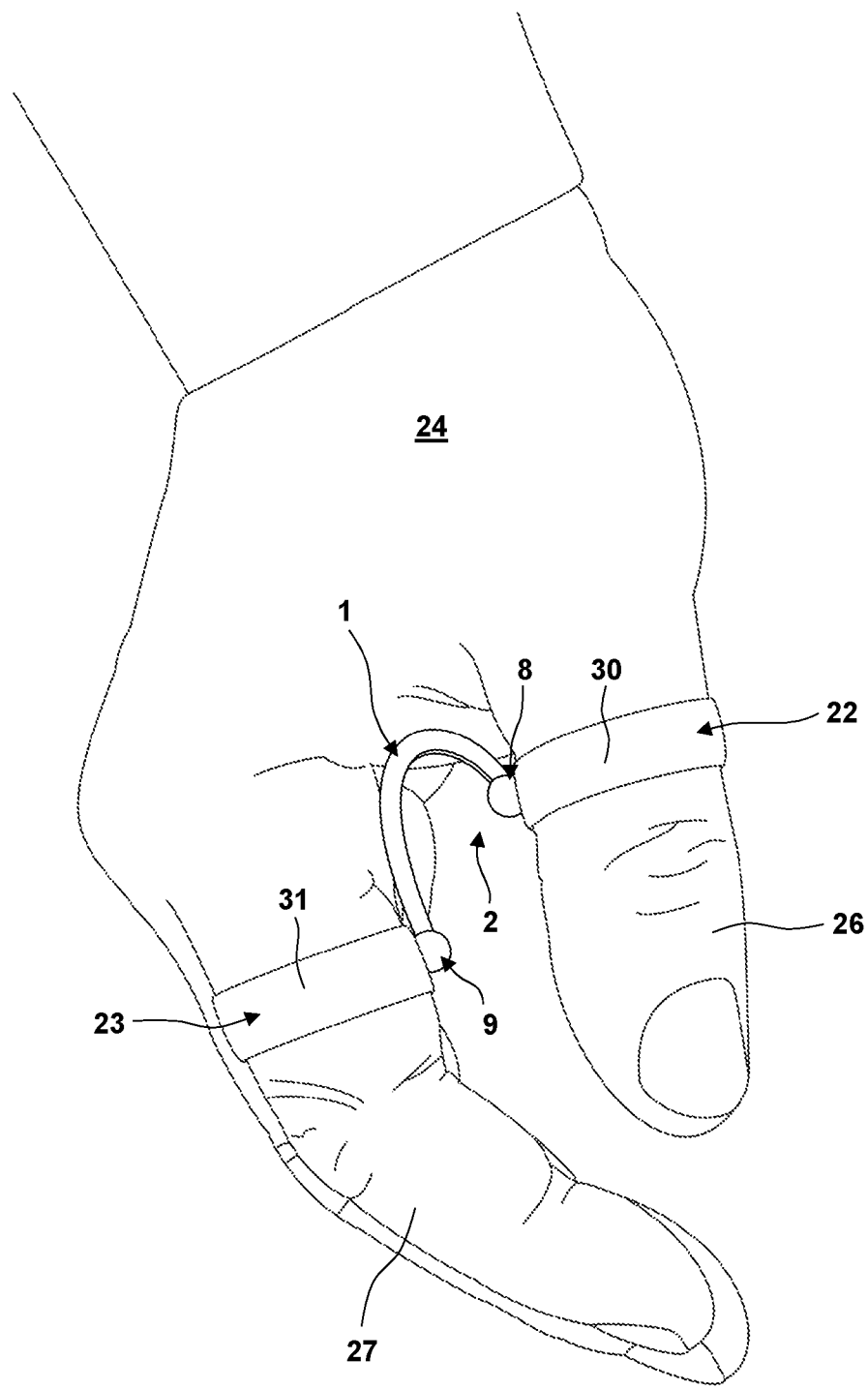

For the embodiment described above, the spreading body 1 contacts the hand (namely the thumb 26, the thumb bow 25 and the pointer finger 27) along its entire extension. In FIGS. 15 and 16 an embodiment is shown wherein this is not the case. Instead, for this embodiment the spreading body 1 is a kind of bridge, junction or clip between the holding devices 22, 23, the spreading body 1 extending between the thumb 26 and the pointer finger 27 without any contact to the thumb bow 25. The spreading body 1 might then have any geometry and might e.g. be embodied as an elastic bow or bending beam or as an elastic pressure rod and/or pulling rod. Here, the connection of the holding devices 22, 23 to the spreading body 1 can be provided by coupling devices 8, 9 which in some cases also form a kind of link or joint so that a pivoting degree of freedom can be provided between the spreading body 1 and the holding devices 22, 23.

FIG. 15 shows the base state wherein the spreading body 1 is not elastically tensioned. Instead, FIG. 16 shows the elastic tensioning of the spreading body 1 due to forces applied by the thumb 26 and the pointer finger 27 for moving the thumb 26 closer to the pointer finger 27.

FIG. 17 schematically shows the force 41 biasing the thumb orthosis 2 (here the spreading body 1) during the use.

In order to quantify the stiffness of the spreading body 1, the end portion 28 of the side leg 3 is oriented horizontally on a support base. The force 41 biases the end portion 28. On the effective line of the force 41 biasing the end portion 28 of the side leg 3 the corresponding counter force 41 biases the side leg 4 of the spreading body 1. If in this case both the force 41 as well as the opening angle 15 changing due to the biasing force 41 are measured, in this way a stiffness (or for a change of the absolute value of the force 41 a stiffness characteristic) of the spreading body 1 can be measured. Preferably, a stiffness of the spreading body 1 is chosen such that with a force 41 of 10 Newton a change of the opening angle 15 of the end portions 28, 29 of the side legs 3, 4 results which is a) 45° (±20° or ±15° or ±10° or ±5°) or
b) 30° (±20° or ±15° or ±10° or ±5°) or
c) 50° (±20° or ±15° or ±10° or ±5°).

The corresponding stiffness behavior might also apply for the application of smaller forces. Here, the stiffness characteristic of the applied force over the opening angle 15 might be linear or might have any non-linear behavior.

Preferably, the spreading body 1 is made of a thermoplastic polyurethane. Here, the spreading body might have a hardness Shore A of 80 (±20 or ±15 or ±10 or ±5) or a hardness Shore A of 90 (±20 or ±15 or ±10 or ±5). However, it is also possible that the spreading body 1 is made of a polyurethane or silicone.

The thumb orthosis 2 can be used for the everyday operation without significantly interfering with the use of the hand 24. It is easy to remove the thumb orthosis 2 from the hand and easy to clean the same. It is also possible that the length of the holding straps 30, 31 can be adapted according to the needs by cutting. It is possible that a plurality of coupling devices 8, 9 (in particular of mushroom heads 10) is dispersed in longitudinal direction or also arranged one besides another. It is e.g. possible that the coupling devices 8, 9, respectively mushroom heads 10, are provided in a kind of double row on the spreading body 1. Excess coupling devices 8, 9 (in particular mushroom heads 10) can also be separated. Differing from the use of one holding strap or two holding straps (the longitudinal extension of this strap or theses straps corresponding to the circumference of the thumb 26, respectively of the pointer finger 27) also a longer holding strap can be used which then extends similar to a spiral or coil around the thumb 26, respectively the pointer finger 27.

The inventive thumb orthosis 2 can be applied and removed in a notably simple way and occupies a small space both when being worn as well as when being stored. By the adjustability the number of required models for the required span of hand sizes can be reduced. It is also possible that the same thumb orthosis can be used for being applied both to the right hand as well as to the left hand.

The inventive thumb orthosis 2 allows a controlled mobilizing of the finger joints of the thumb with a controlled guidance of the thumb saddle and the base joints. The thumb orthosis 2 can preferably be used for a non-inflammatory arthrosis in order to prevent an inflammatory arthrosis.

Preferably, the spreading body 1 extends above the second thumb joint and/or the third pointer finger joint, so that also the regions of the thumb and/or the pointer finger being arranged in front of the second thumb joint and/or of the third finger joint can apply forces to the spreading body 1 and/or these regions are supported and guided by the thumb orthosis 2.

In the case of an arthrosis of the thumb saddle joint there might be a stiffening in the applied state of the thumb due to a contraction of the adduction which has an impact on the ability of the thumb saddle joint to allow a juxtaposition of the thumb and the four long fingers or makes the same impossible. In this case, a gripping process with a pincer grip or precision grip might be impossible.

The thumb orthosis 2 can be named a dynamic thumb orthosis 2 because during the gripping process with a pincer grip 2 or precision grip it is possible to move the thumb and the pointer finger via the thumb orthosis as a hypomochlion. It is possible that when using the thumb orthosis 2 for everyday works and for executing a gripping process the thumb saddle joint is spread and so there is a prophylaxis of an increasing contraction of the adductors or a reduction of a present contraction of the adductors.

Many variations and modifications may be made to the preferred embodiments of the invention without departing substantially from the spirit and principles of the invention. All such modifications and variations are intended to be included herein within the scope of the present invention, as defined by the following claims.

We claim:

1. A thumb orthosis comprising a) a spreading body designed and configured for spreading a thumb and a pointer finger, wherein the spreading body comprises a curved base leg, a first side leg and a second side leg, the first side leg and the second side leg extending from end portions of the curved base leg such that when worn by a user, the first side leg does not extend beyond a first phalanx of the thumb, and the second side leg does not extend beyond a first phalanx of the pointer finger, b) a first holding device comprising one single first holding strap held by a first end portion of the spreading body and designed and configured for holding the spreading body only at the first phalanx of the thumb, c) a second holding device comprising one single second holding strap held by a second end portion of the spreading body and designed and configured for holding the spreading body only at the first phalanx of the pointer finger, d) the thumb orthosis being exclusively held by the first holding device and by the second holding device at a hand of a user wearing the thumb orthosis, e) wherein the one single first holding strap and the one single second holding strap are flexible, elastic or form-stable, f) wherein the one single first holding strap is partially or completely looped around the first phalanx of the thumb, g) wherein the one single second holding strap is partially or completely looped around the first phalanx of the pointer finger, h) wherein the thumb orthosis consists only of the first holding device, the second holding device and the spreading body, the spreading body being an integral one-pieced component having a stable shape that can be elastically deformed, i) wherein the spreading body comprises an elasticity such that it is possible to elastically deform the spreading body by closing forces applied by the thumb and the pointer finger for reducing a distance of the first end portion and the second end portion of the spreading body, j) wherein the spreading body comprises the curved base leg, the first side leg and the second side leg which extend from end portions of the curved base leg, the first side leg and the second side leg diverging with an increasing distance from the curved base leg, and k) wherein a length of at least one of the first side leg and the second side leg of the spreading body is adjustable by removing an outer end of at least one of the first side leg and the second side leg at a predetermined separation point.

2. The thumb orthosis of claim 1, wherein at least one of the one single first holding strap and the one single second holding strap comprises two holding strap portions which extend in opposite circumferential directions from the spreading body around the first phalanx of the thumb or the first phalanx of the pointer finger.

3. The thumb orthosis of claim 2, wherein end portions of the one single first holding strap and one single second holding strap of the holding device can be connected to each other by a connecting device.

4. The thumb orthosis of claim 2, wherein end portions of the one single first holding strap and the one single second holding strap can be connected to each other by a connecting device.

5. The thumb orthosis of claim 1, wherein a length of at least one of the one single first holding strap and the one single second holding strap is adjustable.

6. The thumb orthosis of claim 5, wherein the length can be adjusted by use of a predetermined separation point of the one single first holding strap and the one single second holding strap.

7. The thumb orthosis of claim 1, wherein the first side leg and the second side leg have an opening angle of 60°±20°.

8. The thumb orthosis of claim 1, wherein the spreading body comprises a curved cross-section.

9. The thumb orthosis of claim 1, wherein the spreading body is made of plastic.

10. The thumb orthosis of claim 1, wherein at least one of the first holding device and the second holding device is connected to the spreading body by a coupling device which is releasable.

11. The thumb orthosis of claim 1, wherein at least one of the first holding device and the second holding device is connected to the spreading body by a coupling device which provides a degree of freedom.

12. The thumb orthosis of claim 1, wherein the spreading body comprises a guiding rib designed and configured for guiding an object held or carried by the hand to which the thumb orthosis is applied.

13. The thumb orthosis of claim 1, wherein the spreading body a) comprises a curved base leg, a radius of curvature being 25 mm and b) comprises a first side leg having a length of 11 mm and c) comprises a second side leg having a length of 30 mm and d) has a cross-section with a radius of curvature of 18 mm in a region of the first side leg and e) has a cross-section with a radius of curvature of 37 mm in a region of the second side leg and f) has a cross-section with a radius of curvature of 12 mm in a region of the base leg, or the lengths or radii differ from the lengths or radii specified under a) to f) by less than ±50%.

14. The thumb orthosis of claim 1, wherein a size of at least one of the first holding device and the second holding device is adjustable.

15. The thumb orthosis of claim 1, wherein the length can be adjusted by use of the predetermined separation point of the first and second side leg.

16. The thumb orthosis of claim 1, wherein the first side leg extends away from the curved base leg at an angle in the region of 60°+/−20° relative to the second side leg, wherein the angle is reduced by 45°+/−20° when a force of 10 N is applied to portions of at least one of the firs side leg and the second side leg in a direction towards each other, and wherein the force applied elastically deforms the spreading body by closing forces applied by the thumb and the pointer finger for reducing a distance of tips of the finger and the thumb to create a pinching motion.

17. The thumb orthosis of claim 1, wherein at least one of the first holding device and the second holding device is designed and configured for holding the spreading body at the thumb with a pivoting degree of freedom.

* * * * *